United States Patent [19]

Schectman

[11] Patent Number: 5,080,682

[45] Date of Patent: Jan. 14, 1992

[54] ARTIFICIAL ROBOTIC HAND

[76] Inventor: Leonard A. Schectman, 3742 Boanza Cir., Lantana, Fla. 33462

[21] Appl. No.: 548,237

[22] Filed: Jul. 5, 1990

[51] Int. Cl.$^5$ ............................. A61F 2/54; A61F 2/70
[52] U.S. Cl. ........................................ 623/64; 623/24; 901/21; 901/25; 414/7
[58] Field of Search ..................... 623/63–65, 623/58, 24, 25; 901/21, 25, 28, 39; 414/1, 2, 7; 294/902

[56] References Cited

U.S. PATENT DOCUMENTS 3,694,021 9/1972 Mullen ............................... 414/4 X

FOREIGN PATENT DOCUMENTS 2228390 10/1987 Japan ..................................... 901/25
1333577 8/1987 U.S.S.R. .............................. 901/21

Primary Examiner—Randall L. Green
Assistant Examiner—David H. Willse
Attorney, Agent, or Firm—Malin, Haley, McHale, DiMaggio & Crosby

[57] ABSTRACT

An electro-mechanical grasping device that simulates the movements of a human hand suitable for use as an artificial hand prosthesis that is lightweight, agile and includes a firm grasp. A lightweight platform houses a plurality of very small high torque electrical motors, each having its own linear gear rack, all of which is connected by suitable wire-like actuating member to a plurality of jointed members each of which represents a particular digit of the hand. A stiff cable is connected between all the simulated digits and the gear racks, the cables being mounted through eyelets that act as harness guides for providing the proper strength and movement of each of the digits. Control of the artificial hand and the digits may be through the receipt of myogram signals from the human muscles in the appropriate situation while power is received from a small DC battery.

1 Claim, 2 Drawing Sheets

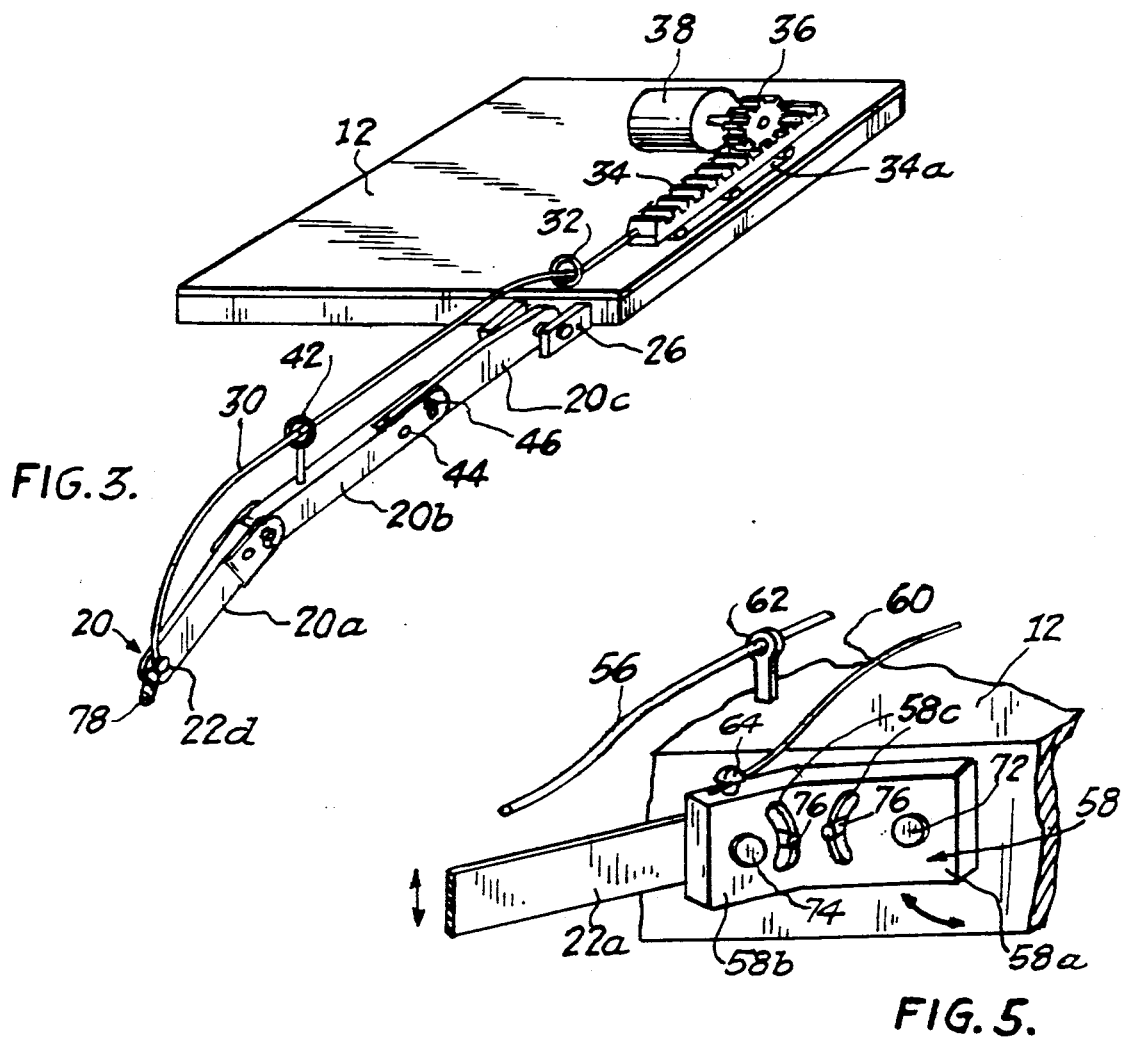
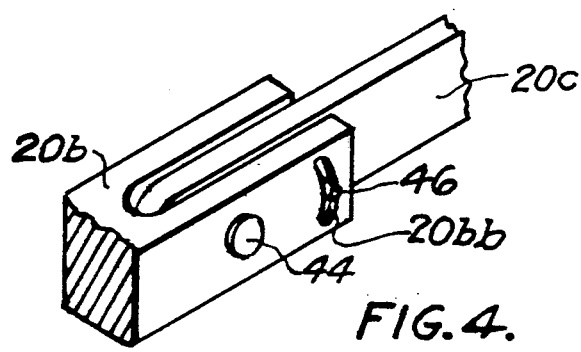

ARTIFICIAL ROBOTIC HAND

BACKGROUND OF THE INVENTION

1. Field of the Invention

An electromechanical grasping device that simulates the movements of a human hand and is suitable for use as an artificial hand prosthesis that includes four jointed movable members simulating the fingers of a hand and a fifth jointed member simulating the thumb, each of said jointed members being individually movable to provide movement comparable to a human hand. The device employs high torque, low current motors which can be controlled by mild pulses from human extremities for controlling movement. A gear rack for each jointed member driven by an individual high torque motor is connected by a stiff wire cable providing individual finger motion allowing rapid movement while retaining firm grasping when employed together.

2. Description of the Prior Art

Many attempts have been made to provide a suitable prosthetic device to be used as a mechanical artificial hand. Because of the unique movements possible of the hand digits including the opposable thumb, the hand has proven to be a very difficult limb to simulate or emulate with the use of an artificial prosthesis. Other considerations when designing an artificial hand are that the device must be comparable in weight to a real hand, have fast movement as in the fingers and the thumb, while still having a firm gripping force to allow practical use of such a prosthesis. U.S. Pat. No. 2,549,716, issued to Simpson, Apr. 17, 1951, shows a mechanical artificial hand that uses springs tensioned against a cable drive mechanism interconnected to mechanically pivoted digits. U.S. Pat. No. 2,859,450, issued to Becker, Nov. 11, 1958, shows an artificial hand mechanism and fingers which also use springs with mechanical leverage connections and rods for actuation. U.S. Pat. No. 3,418,662, issued to Bottomley et al., Dec. 21, 1968, shows a prosthetic hand with the control system activated by electromyogram signals. The mechanical aspect shows a circular gearing mechanism that is connected to a control rod that moves two fingers against a thumb. Finally, U.S. Pat. No. 3,822,418, issued to Yakobson et al., July 9, 1974, shows an artificial hand having a complex electromechanical drive control including a helical gear system with spring actuations.

None of the references shown in the prior art truly duplicate the unique movement of the human hand. Further, they are characterized by complexity in construction and operation and may include weight limitations.

The present invention overcomes these problems by providing a lightweight hand prosthesis that uses individual high torque motors with gear racks connected to stiff cables that can actuate a plurality of hinged digit members quickly with residual rigidity and force generation and which includes movement of the thumb digit member in an opposable direction to the finger digit members.

BRIEF SUMMARY OF THE INVENTION

This invention is comprised of an electromechanical grasping device for use as an artificial hand prosthesis that includes a lightweight hand support platform sized to emulate the metacarpus, said metacarpus platform including four high torque motors mounted thereupon and four gear racks providing a linear gear action from a circular gear connected to each of the lightweight motors. Four moveable digit members are individually connected to the gear racks by cables.

A fifth lightweight high torque motor, gear rack and circular gear are mounted substantially perpendicular to the four finger gear racks and is used for the actuation of a thumb digit member. A sixth high torque motor, gear rack and gear can provide rotation movement of the thumb digit member.

The finger digit members are each constructed of three lightweight aluminum bars hinged together and sized in length to approximate the phalanges for each of the fingers of the hand. Each digit member is connected by a clevis-like joint to the metarcarpus platform extending outwardly from the front edge of the platform. Each hinged joint of the aluminum bar phalanges includes a slot that receives a stop or pin which prevents hyper-extension of each of the phalange bar joints. Further the center phalange for each finger digit member includes a cable harness eyelet that acts as a cable guide and extends above the aluminum bar. The thumb member uses two lightweight aluminum bars hinged together and connected to the metacarpus platform by both a clevis-like joint and a rotational joint.

A stiff cable is connected at one end to each digit member end tip and is routed through cable guides on the metacarpus platform and on the middle phalange bar of each digit, terminating at its opposite end at one end of a linear, moveable gear rack individually provided for each digit member. A similar construction using a stiff cable is connected to the outer end of the thumb phalange bar and to the linear gear rack that moves the thumb bars in a bending motion. An additional cable, linear gear and motor also provide rotational movement of the thumb member. The cables for all digits (fingers and thumb) are sized in length to provide appropriate motion in distance and movement to simulate the movement of each of the finger digits, and the thumb.

Control of the artificial hand and each of the digits is to be through the receipt of myrogram signals from the human muscles in the appropriate situation. Power to the motors is from a small D.C. battery. In considering the control of the invention, certain sensing devices can be included on the fingertips that include pressure sensors to show when an object is being grasped tightly enough to stop the motor actuation and temperature sensors for sensing dangerous temperatures which could set off an alarm. The sensors provide feedback information into the control device while the motors themselves would have control limits for appropriately stopping the motor at the extreme motion paths at each end of the gear rack.

It is an object of this invention to provide an electromechanical device for grasping that emulates and has the capabilities of providing movements that are equivalent to the movement of the human hand including an opposable thumb.

It is another object of this invention to provide an electromechanical grasping device that is non-complex in construction, that is lightweight and provides for extreme dexterity and control of finger and thumb-like extensions to emulate movement of the human hand.

Yet still another object of this invention is to provide an artificial hand prosthesis that includes hinged fingers and a thumb, each having its own individually controlled cable for individual movement while retaining a high grasping force in each finger, and hinged interlocks which prevent hyperextension of each digit.

Another object of the invention is to provide an artificial hand prosthesis that is capable of being utilized in conjunction with human neuromuscular control signals for interaction with the human being to achieve control of the artificial prosthesis.

In accordance with these and other objects which will be apparent hereinafter, the instant invention will now be described with particular reference to the accompanying drawings.

BRIEF DESCRIPTION OF THE DRAWINGS

FIG. 3 shows a perspective view of the invention showing a single finger and the actuating mechanism connected to the metacarpus platform.

FIG. 4 shows a perspective view partially cut away of the phalange hinges as used in the present invention.

FIG. 5 shows a perspective view partially cut away of the thumb hinge as used in the present invention.

PREFERRED EMBODIMENT OF THE INVENTION

Figure 1:
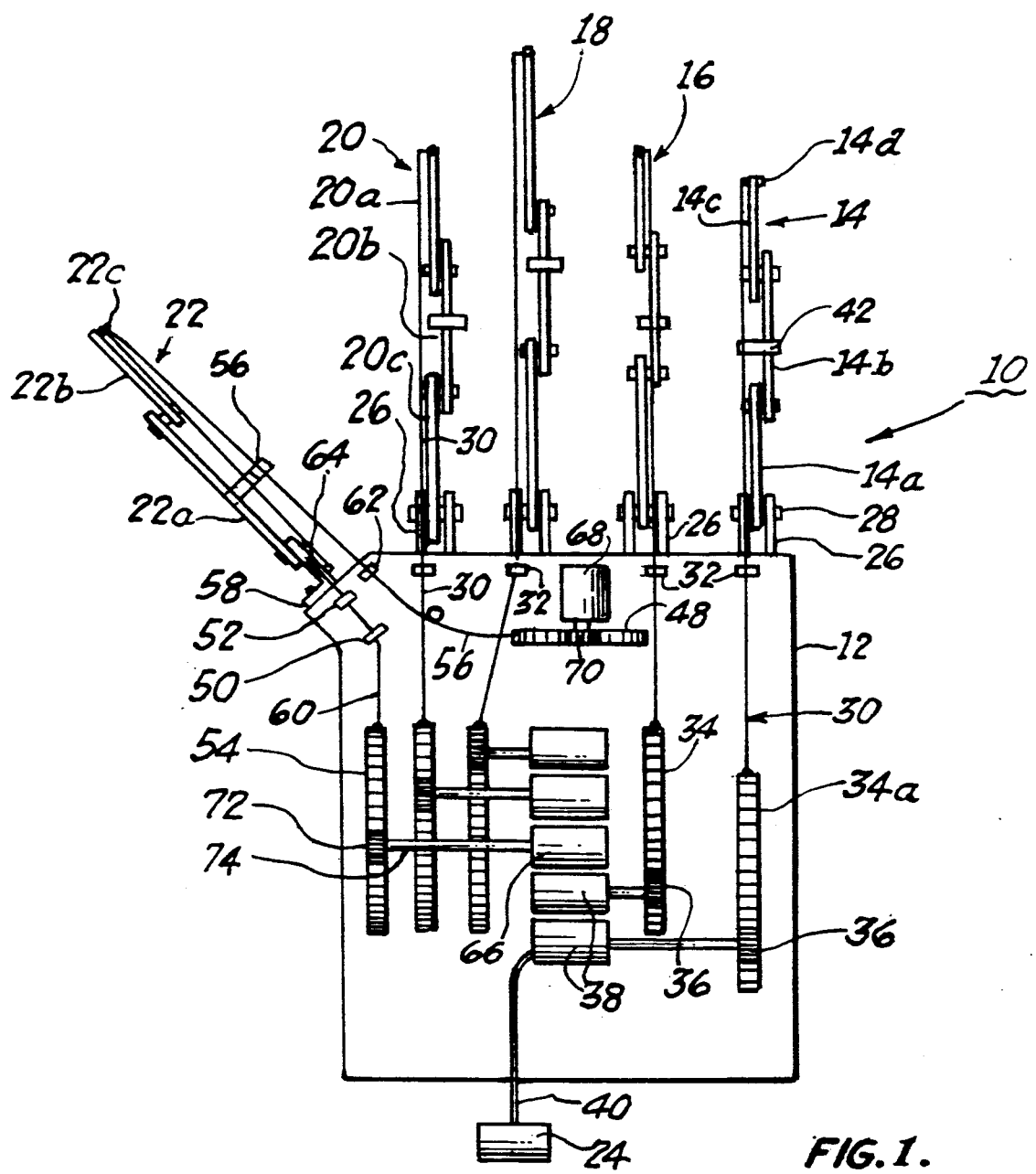
FIG. 1 shows a top plan view of the invention.

Referring now to the drawings and specifically FIG. 1, the present invention is shown generally at 10 comprised of a metacarpus shaped and sized support platform 12 having a series of movable extended hinged members 14, 16, 18 and 20 which emulate the size and movement of human fingers and extended hinged member 22 which emulates movement of the human thumb. Each of the finger extended hinged members 14, 16, 18 and 20 includes three rigid lightweight aluminum support bars hinged together end to end, including support bar 14a, hingably connected to support bar 14b which itself is hinged to support bar 14c which acts as the phalange tip of the finger. Each of the support bars 14a, 14 b and 14 c is sized to emulate the phalanges of the human finger, the entire extended hinged member 14 connected to the metacarpus platform 12 by a clevis connector 26 having a pin 28.

The construction in structure and function of each of the finger-like extended hinged members 14, 16, 18 and 20 are essentially the same and thus the description of the structure for extended hinged member 14 will likewise be the same for each of the remaining fingers 16, 18 and 20.

A relatively stiff yet flexible cable 30 connects the end tip 14d of extended hinged member 14 to a moveable linear gear rack 34a. The cable 30 is threaded through cable guide 32 which is connected near one top edge of platform 12 and a cable guide 42 connected to the middle phalange support bar 14b.

The moveable linear gear rack 34a is connected and supported movably on top of platform 12 and itself is mechanically interconnected to a circular drive gear 36 attached to a high torque, low current drain electric motor 38 mounted near the back portion of platform 12. Connecting and control signal wires 40 are attached to motor 38 and to a control box 24 which may have control inputs using myogram signals from the human body (not shown). Each of the other finger extended hinged members 16, 18 and 20 are constructed and perform in a similar manner as that described for the extended hinged member 14.

The thumb extended hinged member 22, however, is connected to gear racks 48 and 54 and actuating stiff cables 60 and 56 which are threaded through guides 50 and 52, and guides 62 and 56 respectively mounted on platform 12 and on the thumb phalange support bar 22a. The cable 56 terminates at the end tip of thumb phalange 22b with a connector 22c. The moveable linear thumb gear rack 48 is driven by motor 68 and a circular gear 70 as previously described for the finger actuation. Another motor 66, linear gear rack 54, circular gear 72, shaft 74 and cable 60 can provide independent rotation of the thumb extended hinged member.

Figure 2:
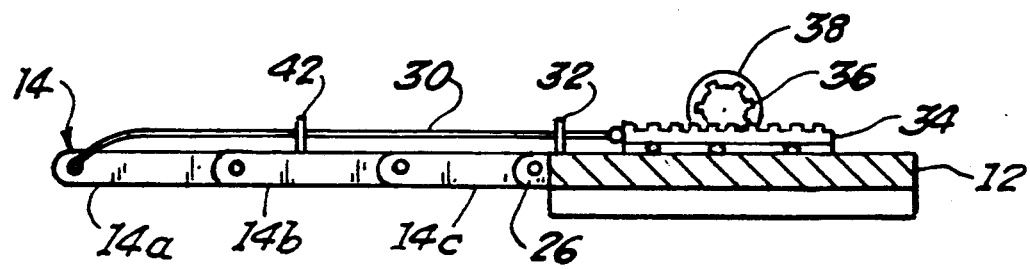
FIG. 2 shows a side elevational view partially in cross section of the present invention.

FIG. 2 shows an example of extended member 14 which acts as the "baby" finger on a right hand made up of three lightweight aluminum support bars 14a, 14b and 14c, each of which is appropriately sized to be comparable to the length of the human finger phalanges for that particular finger. The entire hinged member 14 is held in position and also moved by stiff cable 30 connected to linear gear 34 movably mounted as a gear rack on platform 12. FIG. 2 shows the cable guides 42 and 32 also.

FIG. 3 shows the actuation of the index finger having phalange aluminum support bars 20a, 20b and 20c connected by hinge pins 44 and including a stop pin 46 which prevents hyperextension of either of the phalanges 20a or 20b. A clevis-like hinge 26 connects phalange lightweight aluminum bar 20c to platform 12. As shown in FIG. 3, the gear 34 rides and moves linearly on gear rack 34a providing a linear forward and rear motion by rotation of a circular gear 36 driven by motor 38. Movement of the gear 34 causes cable 30 to move back and forth through the cable guides 32 and 42 providing for articulated motion of the entire finger-like support member 20.

Referring now to FIG. 4, the mechanism to prevent hyperextension of each of the phalange bars such as 20b and 20c is shown comprised of an arcuate slot 20bb near one end of bar 20b that receives stop pin 46 thereby determining the ultimate points of movement as bar 20b pivots around the hinge pin 44 to prevent hyperextension. All of the hinged motion in the phalange joints in the invention can utilize the hyper-extension prevention stops.

Referring now to FIG. 5, the double motion of the thumb extended hinged member is described. The thumb hinged joint is comprised of an angled connector 58 which is essentially a bar that has a bent portion at a predetermined angle thus dividing it into two sections 58a and 58b, with 58a being connected by a pin 72 that permits rotation around pin 72 of the entire bar 58 as shown by the circular arrow. The thumb phalange lightweight bar 22a is likewise rotatably connected with hinge pin 74 to segment 58b on bar 58. Bar 22a can thus move as shown by the arrow in an up and down motion. The actuation of the thumb with two different motions is provided by two different motors 66 and 68 (FIG. 1) as previously described. Specifically, cable 60 attached to bar 58 by connector 64 will provide rotational movement about pin 72 through movement of cable 60 in either direction. Likewise, movement of the extended thumb hinged members beginning with member 22a is provided by cable 56 which is connected to gear rack 70 and motor 68. By providing this double motion and selection of a predetermined angle between the segments 58a and 58b of bar 58, the artificial thumb can be actuated and moved in conjunction with the extended artificial fingers previously described to simulate motion of the thumb realistically, including action as an opposable thumb. The bar 58 may also include slots 58c, which again prevent hyper-extension in conjunction with stop pin 76 as previously described.

Each of the artificial fingers and the artificial thumb as shown can include pressure sensor 78 (FIG. 3) mounted near the ends of the fingertips which can also use wiring that feeds through the actuating cable guides back to a control.

With the use of the present invention in conjunction with myogram signals, the device can be attached using conventional technology to the human limb requiring an artificial hand. With the invention described, it will be possible for extremely articulated movement of the extended hinged members as fingers and thumb for providing realistic grasping and utilization of the artificial hand for providing great realism to the user. With the aid of microprocessor technology, other control devices could also be used with the invention especially in view of the lightweight construction and the use of low current, high torque motors which can be supplied by battery power attached to the platform or conveniently carried by the user.

The instant invention has been shown and described herein in what it is considered to be the most practical and preferred embodiment. It is recognized, however, that departures may be made therefrom within the scope of the invention and that obvious modifications will occur to a person skilled in the art.

What I claim is:

1. An electromechanical grasping device for simulating the movement of a human hand for use as an artificial hand prosthesis comprising:

support platform sized to resemble a human metacarpus and having a first end and a first side next to said first end;

first, second, third and fourth extended hinged members having end tips and movably connected to simulate the movement of human fingers to said first end of said support platform, each of said extended hinged members including first, second and third bars hingeably joined together from end to end;

fifth extended hinged member positioned and sized to simulate the movement of a human thumb movably connected to one side of said support platform;

plurality of linear gear racks attached and movably positioned on said support platform;

plurality of high torque motors each mounted on said support platform and each mechanically connected to a different one of said gear racks for providing individual linear movement of said gear racks;

stiff wire individual cables connecting each of said gear racks independently to a different end tip of said first, second, third and fourth extended hinged members;

cable guide means connected to each of said first, second, third and fourth hinged members for receiving and guiding said cables;

means for controlling said linear gear racks connected to each of said motors;

said first, second, third and fourth extended hinged members connected to one end of said support platform are sized as the digits in a human hand, and located relative to said support platform to approximate the location of human fingers;

said first, second and third bars sized to correspond to the phalanges in the fingers of a human hand;

said fifth extended hinged member having an intermediate support bar and an end tip bar connected together and movably rotatably connected to said first side of said support platform;

a fifth extended member connecting bar having first and second portions that are angularly disposed to each other;

a first hinge connecting one portion of said fifth member connecting bar to one side of said support platform to provide rotational movement, and a second hinge connected to said intermediate support bar whereby the fifth extended member can move rotationally relative to said first and second hinge joints;

said cable means including a first cable connected to said fifth member connecting bar and a second cable connected to the end tip bar;

said first, second and third bars including stopping means to limit the distance of rotational movement;

whereby the first, second, third and fourth hinged members can be individually moved to positions simulating human finger movement through the action of said cables and cable guides attached to said first, second, third and fourth hinged members and said fifth extended member can be moved by said two cables and cable guide means to positions simulating movement of the human thumb.

* * * * *